US006229605B1

(12) United States Patent
Benedict

(10) Patent No.: US 6,229,605 B1
(45) Date of Patent: May 8, 2001

(54) EVAPORATIVE LIGHT SCATTERING DEVICE

(75) Inventor: Mark C. Benedict, Arlington Heights, IL (US)

(73) Assignee: Alltech Associates, Inc., Deerfield, IL (US)

( * ) Notice: Subject to any disclaimer, the term of this patent is extended or adjusted under 35 U.S.C. 154(b) by 0 days.

(21) Appl. No.: 09/523,108

(22) Filed: Mar. 10, 2000

(51) Int. Cl.[7] .................................................... G01N 21/00
(52) U.S. Cl. .......................... 356/339; 356/37; 73/864.81
(58) Field of Search ..................................... 356/336, 337, 356/338, 339, 340, 341, 342, 36, 37, 432, 437; 73/864.81, 864.85, 61.68, 61.69, 61.71; 250/222.2, 576

(56) References Cited

U.S. PATENT DOCUMENTS 4,162,849 * 7/1979 Huber ..................................... 356/36
4,894,529 * 1/1990 Borden et al. ....................... 356/338
4,958,529 9/1990 Vestal .
5,807,750 9/1998 Baum et al. .
5,903,338 * 5/1999 Mavliev et al. ....................... 356/37
5,939,648 * 8/1999 Phan ................................. 73/864.81
6,011,259 * 1/2000 Whitehouse et al. ................ 250/287
6,122,055 * 9/2000 O'Donohue et al. ................ 356/338
6,151,113 * 11/2000 O'Donohue et al. ................ 356/338

OTHER PUBLICATIONS

Polymer Laboratories article entitled "LC Detection for the New Millennium, " regarding a PL–ELS 1000, Evaporative Light Scattering Detector, undated (8 pages).

SEDEX 55 Evaporative Light Scattering Detector Instruction Manual, Licence ANVAR–Unversity of Orléans, 84–05–033 (34 pages).

DDL 31 User's Instruction Manual, Version 2.0 (GB), Sep. 1996, EUROSEP Instruments, France, (49 pages).

* cited by examiner

*Primary Examiner*—Hoa Q. Pham
(74) *Attorney, Agent, or Firm*—Brinks Hofer Gilson & Lione

(57) ABSTRACT

The present invention is directed to a device for evaporative light scattering detection that can be used for a wide range of sample types and mobile phases. The device may be quickly converted between a single flow and a split flow configuration through the use of a retractable impactor.

11 Claims, 4 Drawing Sheets

EVAPORATIVE LIGHT SCATTERING DEVICE

BACKGROUND OF THE INVENTION

Evaporative light scattering detection is a method of detecting samples that have been previously separated in various chromatography methods such as, for example, High Performance Liquid Chromatography (HPLC), Gel-Permeation Chromatography (GPC), High Performance Centrifugal Partition Chromatography (HPCPC), Field Flow Fractionation (FFF), and Supercritical Fluid Chromatography (SFC). Evaporative light scattering detection is preferably used when the sample components (e.g., components to be detected) have lower volatility than the mobile phase. A wide variety of sample types can be detected in evaporative light scattering detection. Such sample types include, for example, lipids, triglycerides, surfactants, polymers, underivatized fatty and amino acids, carbohydrates and pharmaceuticals.

Generally, evaporative light scattering detection involves four main steps: 1) nebulization of the chromatography effluent, (which consists of the mobile phase and the sample), into an aerosol of particles, 2) evaporation of the mobile phase, 3) directing a light beam at the dry sample particles to scatter the light, and 4) detection of the scattered light. The amount of sample is determined based upon on how much light is scattered. There are two principal types of devices used in evaporative light scattering detection known in the art. In the first type (the "single flow" design), the nebulized chromatography effluent is immediately introduced into a heated drift tube where the mobile phase is evaporated. The sample particles are then flowed from the heated drift tube to an optical cell where light scattering and detection occurs. One such example of this type of device (the Alltech Model 500 ELSD) is sold by the assignee of this application, ALLTECH ASSOCIATES, INC. Details concerning the design and operating parameters for such a device are disclosed in the Operating Manual for the Alltech Model 500 ELSD, which is incorporated herein by reference.

In the second type of device, (the "split-flow" design), the nebulized chromatography effluent is first flowed through a nebulization chamber before entering the heated drift tube. In the nebulization chamber, the nebulized chromatography effluent is split, namely, the larger droplets are eliminated by condensation/impaction on the walls of the nebulization chamber. This condensate is drained to waste. Only the smaller nebulized droplets are subsequently flowed to the heated drift tube where the mobile phase (which is now free of the larger droplets) is more easily evaporated. Thereafter, the sample particles are flowed to the optical cell for light scattering and detection. Devices of this design type are available from, for example, POLYMER LABORATORIES, SEDERE or EUROPSEP INSTRUMENTS.

The above-described design types have particular advantages depending on the mobile phase and the sample type. The single flow design is preferred for use in applications involving the detection of relatively non-volatile samples in relatively volatile organic mobile phases. Moreover, because the entire sample enters the optical cell in this design, response and sensitivity is maximized.

However, the single flow design is not especially preferred when detecting relatively volatile samples in relatively non-volatile mobile phases (such as aqueous mobile phases). Highly aqueous mobile phases generally require higher evaporation temperatures. If the sample is volatile at these higher evaporation temperatures, sample loss is incurred during the evaporation step resulting in poorer sensitivity. By using the split-flow design (i.e., passing the chromatography effluent through a nebulization chamber to remove the larger droplets of mobile phase prior to the heated drift tube), the evaporation temperature of the mobile phase can be reduced. Thus, the mobile phase may be evaporated at a lower temperature in the drift tube, which leads to less sample loss from evaporation. In other words, by removing the larger droplets, a smaller and more uniform particle size distribution is achieved in the mobile phase, which enables evaporation of the mobile phase at lower evaporation temperatures.

However, for relatively non-volatile sample types in relatively volatile organic mobile phases, the split-flow design is generally less preferred because (1) loss of the relatively non-volatile sample during evaporation at lower temperatures of the relatively volatile mobile phase is not a concern (2) the relatively non-volatile sample may be lost during the splitting of the chromatography effluent in the nebulization chamber. Another problem with devices of the split-flow design is that the split ratio of the sample (i.e., the amount that goes to waste versus the amount that is ultimately detected) is affected by, among other things, the laboratory temperature. In other words, fluctuations in laboratory temperatures may lead to fluctuations in droplet size in the nebulized chromatography effluent. Thus, as ambient and/or laboratory temperatures fluctuate, the split ratio and corresponding reproducibility of sample detection may vary from run to run.

As is evident from the above-discussion, depending on the mobile phase and the sample type being detected, one evaporative light scattering detection design and method is advantageous over the other. However, laboratories often work with both aqueous and organic mobile phases and various sample types with different volatilities. Ideally, laboratories would have available both design types for evaporative light scattering detection. However, in order to have this benefit, the laboratory would need to purchase two separate devices, which can be expensive. It would be advantageous and constitute an improvement in the art if an evaporative light scattering detection device and system were developed which could be quickly and inexpensively converted between the single flow and split flow configuration.

To address this need, Applicants previously developed a device and system for easy and quick conversion between the single flow and the split flow configuration. That system and design is disclosed in co-pending application Ser. No. 08/932,262, which is assigned to the assignee of this application. The disclosure of 08/932,262 is fully incorporated herein by reference. Although the system and device disclosed in this co-pending application fulfills the above need, a disadvantage associated with that system and device is that the nebulizer must be removed, a flow splitting adaptor installed and the nebulizer replaced when converting from the single flow to the split flow configuration. The present invention avoids the need of removing the nebulizer and inserting a flow splitting adaptor when converting from the single flow to the split flow configuration.

SUMMARY OF THE INVENTION

According to one aspect of the present invention, a device for evaporative light scattering detection is provided that may be quickly and easily converted between the single flow and split flow configurations. The device comprises a nebulizer, a drift tube in flow communication with the nebulizer wherein the drift tube has a drain outlet and a retractable impactor located downstream in the direction of flow from the drain outlet, a light source positioned downstream of the drift tube and a detector.

DETAILED DESCRIPTION OF THE PREFERRED EMBODIMENTS

Figure 1:
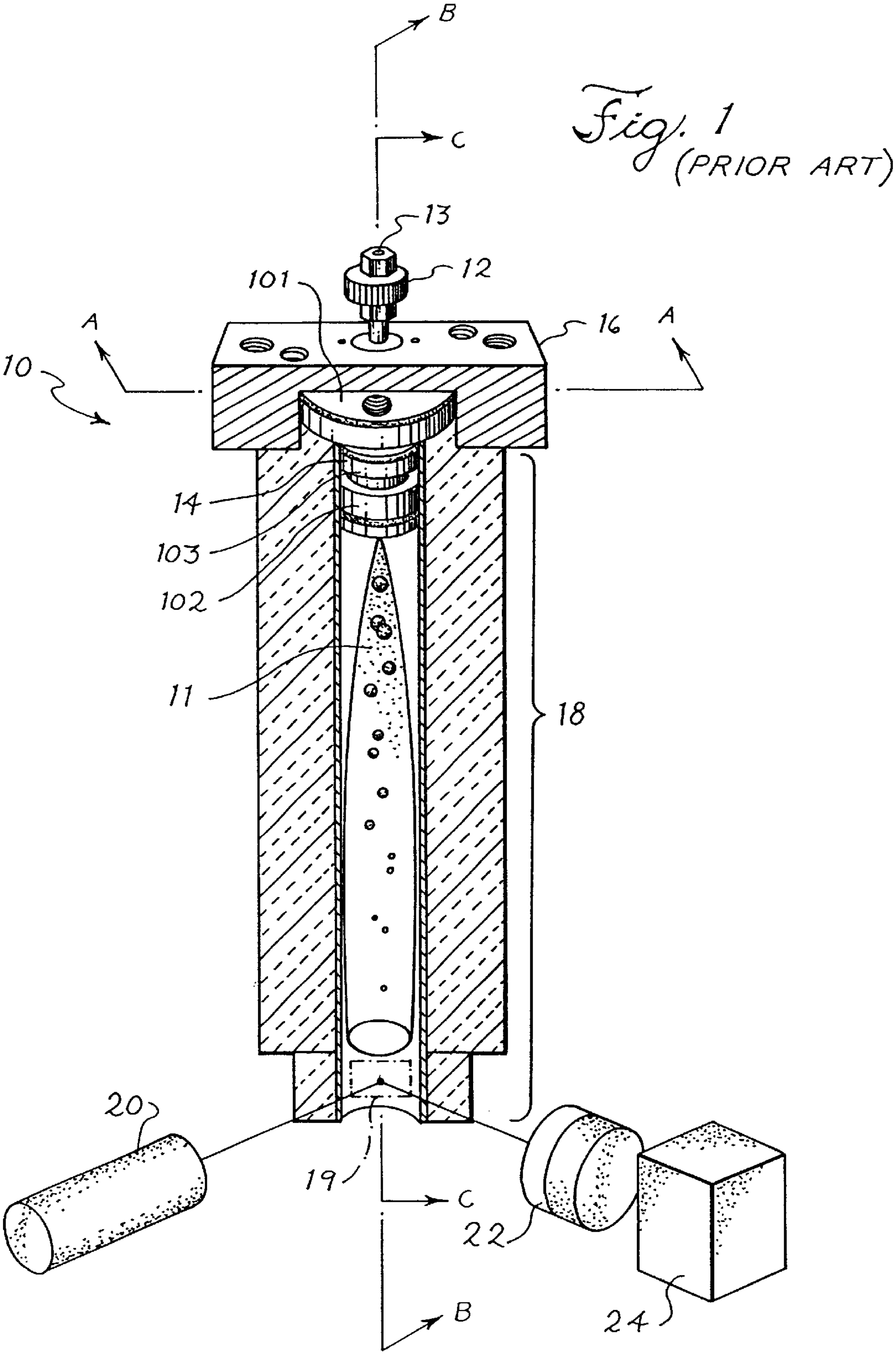
FIG. 1 is a chematic diagram illustrating the principles of operation of an evaporative light scattering detection device.

FIG. 1 illustrates an evaporative light scattering detection device of the single flow configuration. FIG. 1 provides an overview of the principal of operation of an evaporative light scattering detection device 10. The evaporative light scattering device 10 has a connector 12. The connector 12 provides a fluid connection between the chromatography column (not shown) and the evaporative light scattering device 10. The connector 12 is preferably made from stainless steel and is threadingly engaged to nebulizer bracket 16. Chromatography effluent is flowed into the evaporative light scattering device 10 through channel 13 in connector 12. Nebulizer bracket 16 removably attaches nebulizer 14 to drift tube assembly 18. The nebulizer 14 contains a nebulizer needle (not shown). The drift tube assembly 18 surrounds a central heated drift tube channel 11. Finally, a laser light source 20, a photodetector 22 and amplifier 24 are provided.

In operation, and with reference to FIG. 1, the chromatography effluent is flowed through connector 12 to nebulizer 14. The chromatography effluent is directed through the nebulizer needle (not shown). Upon exiting the nebulizer needle, the chromatography effluent is impacted by nebulizer gas to form an aerosol of droplets, preferably of generally uniform size. The nebulizing gas may include any gas that is inert to the sample such as helium, carbon dioxide, air or nitrogen, and is preferably nitrogen.

The nebulized chromatography effluent is then flowed through channel 11 in the drift tube assembly 18. In channel 11, the mobile phase is evaporated leaving behind the relatively non-volatile sample particles. The sample particles are flowed through channel 11 to the light scattering zone 19 for detection. A light source 20 emits light, which the sample particles scatter. The scattered light is then detected at the photodetector 22. The photodetector 22 then produces a signal, which is sent to an amplifier 24 though analog outputs in the photodetector.

The light source 20 is preferably a Class IIIA laser product with 650 nm laser diode, 5 mW maximum power, collimating optics, and polarized. A preferred laser light source is available from COHERENT, as part no. VLM3-5L. The photodetector 22 is preferably made from a silicon photodiode. A preferred photodetector 22 is available from HAMAMATSU, as part no. S2386-8K. The photodetector 22 is preferably located at a 90-degree angle from the light source 20. A light trap (not shown) is also preferably located at a 180-degree angle from the light source 20 to collect any light not scattered by the sample particles in the aerosol stream. After detection in the detection zone, the sample particles are flowed to waste. Preferably the exhaust is flowed to a fumed hood or other ventilation device located close to the detector to remove the detector exhaust from the laboratory.

In operation, the nitrogen nebulizing gas is preferably regulated from 45–80 psig with 99.9% purity or better. A stable gas flowrate and pressure are necessary for reproducible results. The gas is preferably free of contaminants, such as oil, water, particulate or any other non-volatile substances. The droplet size in the nebulized chromatography effluent may be regulated by varying the flow rate of either the chromatography effluent and/or the nebulizing gas. The lower the flow rate of the chromatography effluent, the less gas and heat necessary for nebulization and subsequent evaporation.

Figure 2:
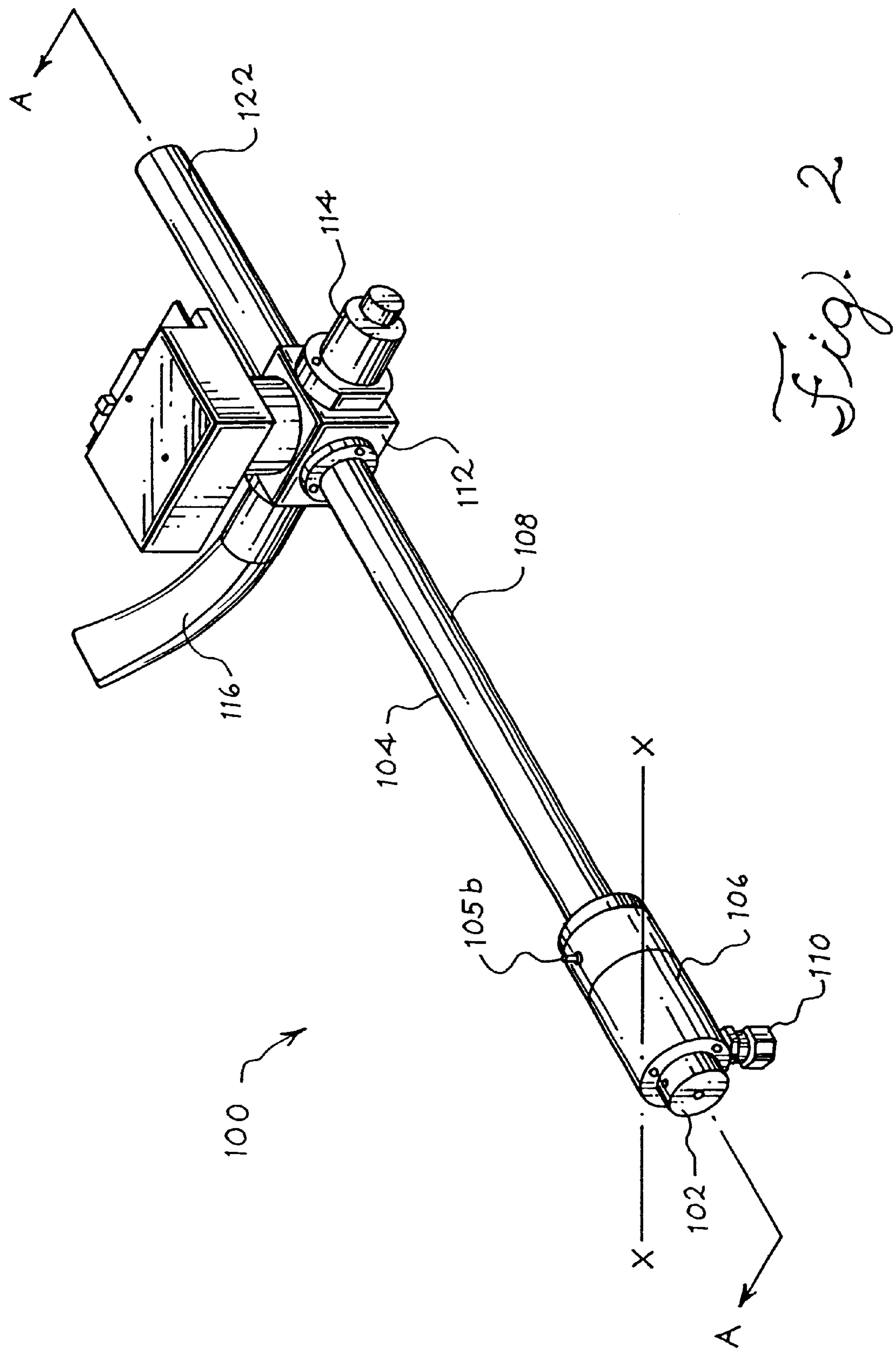
FIG. 2 is a perspective view of a preferred embodiment of the device of the present invention.

With reference to FIG. 2, a preferred embodiment of the evaporative light scattering device 100 of the present invention is illustrated. The device comprises a nebulizer 102. The nebulizer is preferably as disclosed in co-pending application Ser. No. 08/932,262 and is available from ALLTECH ASSOCIATES, part no. 600514. Downstream in the direction of flow from the nebulizer is a tube 104. The drift tube may preferably be constructed as set forth in co-pending application Ser. No. 08/932,262. The drift tube has two sections, a nebulizer block 106 and a mid-section 108. The nebulizer block 106 connects the nebulizer 102 to the drift tube. The nebulizer 102 is in flow communication with the drift tube 104. The drift tube 104 further has a drain outlet 110, which is preferably located on the nebulizer block 106. The drift tube also has a retractable impactor 105, which is also preferably located on the nebulizer block 106. The impactor 105 preferably comprises a planar, solid section 105*a* mounted on a pin 105*b*. By retractable, it is meant that the planar section 105*a* may be rotated from a position where the face of the planar section is parallel to the direction of fluid flow (parallel mode) to a position in which the face of the planar section is at a 90 degree angle to the path of flow (perpendicular mode) through the drift tube 104. When in the perpendicular mode, the planar section provides an impact surface for the nebulized mobile phase particles to strike, which leads to condensation of those particles. By directing the mobile phase against the impactor in this fashion, a portion of the mobile phase undergoes condensation and is separated from the nebulized sample particles. Moreover, because the drift tube is positioned at an angle such that the drain outlet is below the impactor relative a plane X—X through the device between the impactor and the drain outlet, condensed mobile phase is removed from the device by gravity through the drain outlet 110.

Preferably, the planar section 105*a* is tapered (see FIG. 4) and is constructed from TEFLON coated stainless steel. The outer edges of the planar section 105*c* and *d* generally correspond to the contour of the inner wall 104*a* of the drift tube. The impactor pin is preferably constructed from stainless steel. In the perpendicular mode, the impactor preferably blocks about 70% of the flow path in the plane through the drift tube in which the impactor planar section 105*a* resides. In the parallel mode, the impactor preferably blocks about 18% of the flow path in the plane through the drift tube in which the impactor planar section 105*a* resides. However, because the impactor is preferably tapered (see FIG. 5), most of the mobile phase and sample will flow past the impactor when it is in its parallel mode. The impactor is preferably rotated between the parallel and perpendicular modes by a motor (not shown), such as a direct drive solenoid motor. However, the impactor may be rotated manually if desired. Also, rotation of the impactor may be programmed by the user and driven by logic.

Alternatively, the device may be constructed such that the impactor is inserted and retracted from the fluid flow channel instead of rotated between the perpendicular and parallel modes as described above. Thus, the impactor may be inserted into the flow channel of the drift tube and positioned in the perpendicular mode and removed from the flow channel all together by appropriate means. The term "retractable" is meant to include the above described impactor that may be rotated between the perpendicular and parallel modes as well as to an impactor that may be inserted into the flow channel and positioned in the perpendicular mode and removed from the flow channel all together.

Additionally, the shape of the impactor may be varied. The only critical aspect of the impactor is that it provide a sufficient impact surface for the nebulized mobile phase when the device is in the split flow configuration and that this impact surface may be easily removed from the path of flow for converting to the single flow configuration.

Figure 3:
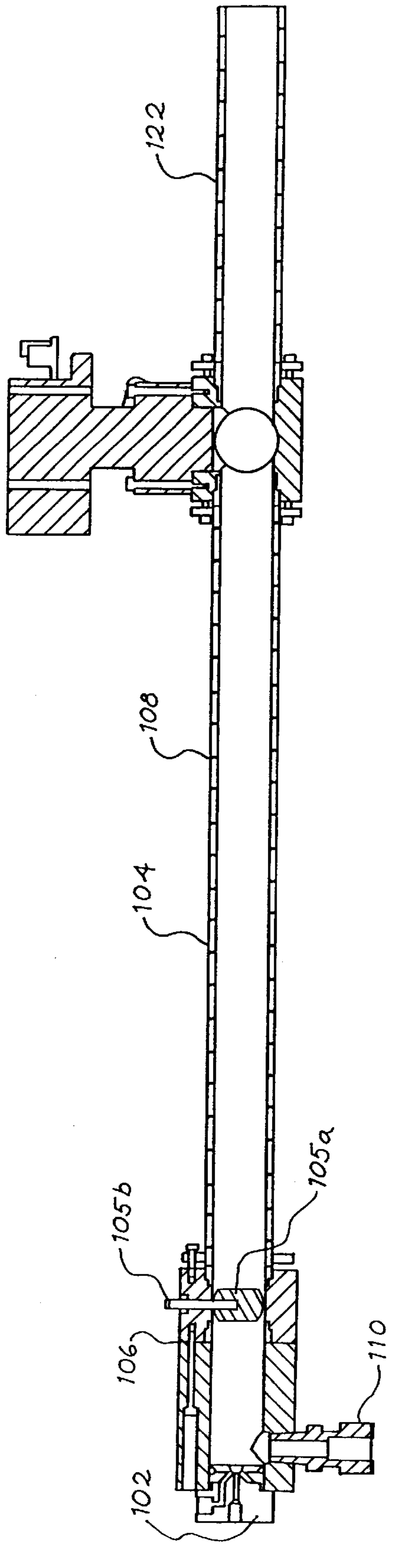
FIG. 3 is a cross-section along line A—A of FIG. 2 with the retractable impactor in the parallel mode.
Figure 4:
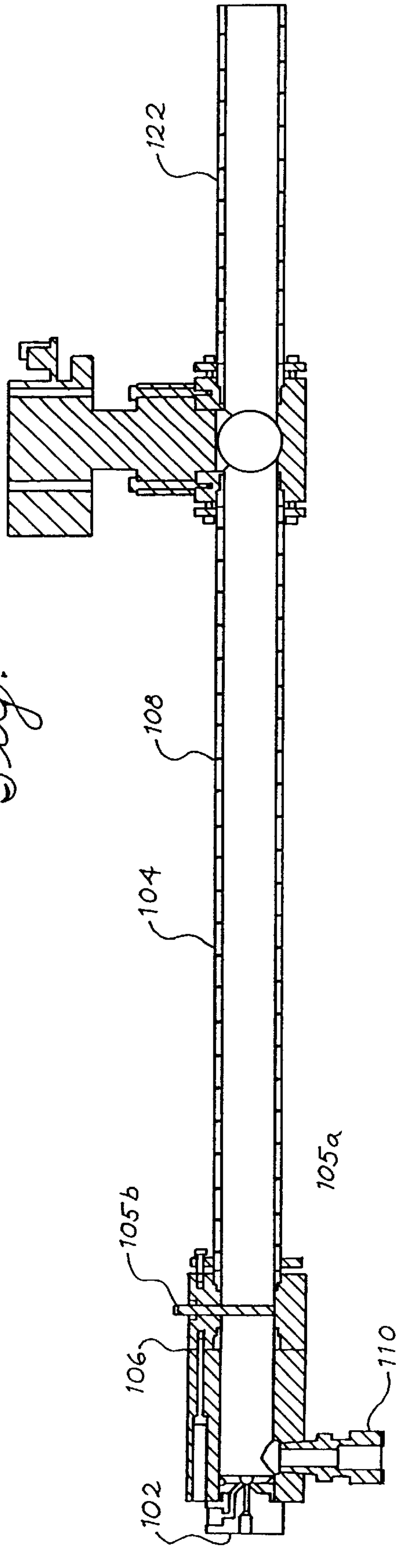
FIG. 4 is a cross-section along line A—A of FIG. 2 with the retractable impactor in the perpendicular mode.

With further reference to FIGS. 2–4, the drift tube 104 is in flow communication with an optics block 112. The optics block comprises a light source 114, which is preferably a laser available from COHERENT as part VLMIII-5L, and a light trap 116. The light trap is preferably an insulated block of black anodized aluminum of suitable curvature to funnel light to its end. The device further comprises a detector 118, which comprises a photo diode and amplifier available from ELECTRO-OPTICAL SYSTEMS as part no. S-050-E8. The drift tube 104 and optics block 112 are in flow communication with an exhaust tube 122.

In the single flow configuration, the impactor 105 is in the parallel mode (FIG. 3). The sample and mobile phase are introduced into the nebulizer 102 where the sample and mobile phase are nebulized. The sample and mobile phase particles are then flowed to the drift tube where the mobile phase is evaporated. The sample particles are then flowed to the optics block where the sample particles are detected. The sample particles are then flowed to the exhaust tube 122 and then to waste.

The device may be quickly and easily converted to the split flow configuration by placing the impactor in the perpendicular mode (FIG. 4). In this mode, sample and mobile phase are nebulized in the nebulizer. The nebulized sample and mobile phase strike the planar section 105*a* of the impactor, which removes a portion of the nebulized mobile phase (and possible a portion of the sample) from the flow stream by condensation. This condensate is flowed out of the drift tube through drain outlet 110. The remaining portion of the sample and mobile phase is flowed through the drift tube where the mobile phase is evaporated. The sample particles are then flowed to the optics block where the sample is detected.

In a preferred aspect of the invention, the device has four zones in which the temperature is controlled independently of the other zones. Thus, the first zone is located between the nebulizer 102 and the impactor 105. The second zone is located between the impactor 105 and the optics block 112. The third zone is the optics block 112. The fourth zone is the exhaust tube. The zones are heated by using heat tape embedded in the nebulizer block, drift tube, optics block and the exhaust tube as well known in the art. Moreover, each of these zones is connected to their own power source for independent temperature control. As those skilled in the art will appreciate, optimum temperature conditions for the particular sample and mobile phase are more easily achieved by dividing the device into four temperature zones.

Figure 6:
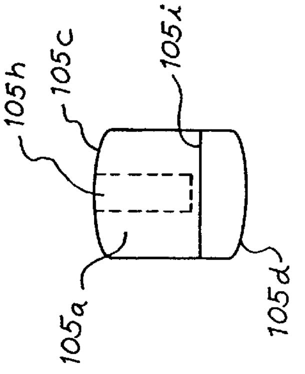
FIG. 6 is top plan view of the retractable impactor.
Figure 5:
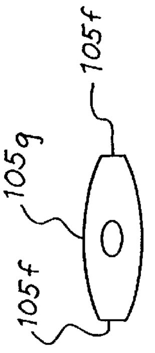
FIG. 5 is an end perspective view of the retractable impactor.

According to a most preferred embodiment of the present invention, the evaporative light scattering device may have the following dimensions. The distance between the tip of the nebulizer needle to the end of the exhaust tube 122 is 23.627 inches. The distance from the tip of the nebulizer needle to the impactor 105 is 2.594 inches. The nebulizer block 106 is 3.574 inches in length. The mid-section of the drift tube 104 is about 13 inches in length. The length of the exhaust tube is 4.388 inches. The internal diameter of the drift tube 104 is about 0.87 inches. The impactor 105 preferably has the following dimensions. With reference to FIGS. 5 and 6, edges 105*f* are about 0.016 inches in length. The impactor has a thickness of about 0.091 inches along line 105*g*. Bore 105*h* has an internal diameter of about 0.276 inches for receiving mounting needle 105*b*. The impactor 105 further has a width of about 0.552 inches along line 105*i*.

As those skilled in the art will appreciate, modifications may be made to the foregoing embodiments without departing from the invention, which is defined by the following claims.

What is claimed is:

1. A device for evaporative light scattering detection wherein a sample to be detected is flowed through the device, the device being capable of easy conversion between a single flow configuration and a split flow configuration, the device comprising:

a nebulizer;

a drift tube in flow communication with the nebulizer, the drift tube comprising a drain outlet and a retractable impactor positioned downstream in the direction of flow from the nebulizer;

a light source positioned downstream of the drift tube; and a detector.

2. The device of claim 1 wherein the retractable impactor has a perpendicular mode and a parallel mode and is converted between these two modes by rotation.

3. The device of claim 2 wherein the drift tube is positioned such that the drain outlet is located upstream of the impactor and, with respect to a horizontal plane bisecting the drift tube at a point between the drain outlet and the impactor, below the impactor.

4. The device of claim 3 wherein the drift tube comprises a nebulizer block and a mid-section, the drain outlet and impactor positioned on the nebulizer block.

5. The device of claim 4 further comprising an exhaust tube positioned downstream in the direction of flow from the detector.

6. The device of claim 5 wherein the device has four zones in which the temperature is independently controlled, the first zone located between the nebulizer and the impactor, the second zone positioned between the impactor and detector, the third zone located at an optics block, and the fourth zone positioned in the exhaust tube.

7. The device of claim 2 wherein the impactor comprises a planar section mounted on a pin.

8. The device of claim 7 wherein the impactor is rotated between the parallel mode and the perpendicular mode by a motor.

9. The device of claim 8 wherein the motor is actuated by logic.

10. A device for evaporative light scattering detection wherein a sample to be detected is flowed through the device, the device being capable of easy conversion between a single flow configuration and a split flow configuration, the device comprising:

a nebulizer;

a drift tube in flow communication with the nebulizer, the drift tube comprising a drain outlet positioned downstream in the direction of sample flow from the nebulizer and a retractable impactor positioned downstream in the direction of flow from the drain outlet, wherein the drain outlet is positioned below the impactor relative a horizontal plane bisecting the drift tube between the drain outlet and the impactor a light source positioned downstream of the drift tube;

a detector; and the retractable impactor further comprising a planar surface that may be rotated between a parallel mode and a perpendicular mode relative the path of flow through the drift tube.

11. The device of claim 10 wherein the planar surface of the impactor is mounted on a pin.

* * * * *

UNITED STATES PATENT AND TRADEMARK OFFICE
CERTIFICATE OF CORRECTION

PATENT NO. : 6,229,605 B1
DATED : May 8, 2001
INVENTOR(S) : Bart C. Benedict

It is certified that error appears in the above-identified patent and that said Letters Patent is hereby corrected as shown below:

Title page,
Item [75], delete "Mark C. Benedict" and substitute -- Bart C. Benedict -- in its place.

Signed and Sealed this

Eighth Day of January, 2002

Attest:

JAMES E. ROGAN

*Attesting Officer* *Director of the United States Patent and Trademark Office*